US 6,652,876 B2

(12) United States Patent
Radloff et al.

(10) Patent No.: US 6,652,876 B2
(45) Date of Patent: Nov. 25, 2003

(54) ACTIVE SUBSTANCE PATCH, KIND TO THE SKIN, FOR TRANSDERMAL ADMINISTRATION OF NONSTEROIDAL ANTIRHEUMATICS

(75) Inventors: Detlev Radloff, Hamburg (DE); Matthias Wasner, Hamburg (DE)

(73) Assignee: Beiersdorf AG, Hamburg (DE)

( * ) Notice: Subject to any disclaimer, the term of this patent is extended or adjusted under 35 U.S.C. 154(b) by 63 days.

(21) Appl. No.: 09/745,613

(22) Filed: Dec. 21, 2000

(65) Prior Publication Data

US 2002/0119185 A1 Aug. 29, 2002

(30) Foreign Application Priority Data

Jan. 28, 2000 (DE) .......................................... 100 03 767

(51) Int. Cl.⁷ ............................................... A61L 15/16
(52) U.S. Cl. ........................ 424/448; 424/484; 424/486
(58) Field of Search ................................ 424/448, 449, 424/484, 486

(56) References Cited

U.S. PATENT DOCUMENTS

| 3,339,546 | A | | 9/1967 | Chen et al. | |
|---|---|---|---|---|---|
| 4,186,258 | A | | 1/1980 | Schmidt, III et al. | |
| 4,231,369 | A | | 11/1980 | Sorensen et al. | |
| 4,393,080 | A | | 7/1983 | Pawelchak et al. | |
| 4,477,325 | A | | 10/1984 | Osburn | |
| 4,559,222 | A | | 12/1985 | Enscore et al. | |
| 4,627,852 | A | | 12/1986 | von Bittera et al. | |
| 4,661,104 | A | | 4/1987 | von Bittera et al. | |
| 4,668,232 | A | | 5/1987 | Cordes et al. | |
| 4,818,540 | A | * | 4/1989 | Chien et al. | ................. 424/448 |
| 5,028,435 | A | * | 7/1991 | Katz et al. | ................... 424/484 |
| 5,120,546 | A | * | 6/1992 | Hansen et al. | ............... 424/449 |
| 5,262,216 | A | | 11/1993 | Popat et al. | |
| 5,318,960 | A | * | 6/1994 | Toppo | .......................... 514/159 |
| 5,350,581 | A | * | 9/1994 | Kochinke | ................... 424/443 |
| 5,508,038 | A | | 4/1996 | Wang et al. | |
| 5,527,536 | A | | 6/1996 | Merkle et al. | |

FOREIGN PATENT DOCUMENTS

| DE | 3347277 A1 | | 7/1985 | |
|---|---|---|---|---|
| DE | 3347278 A1 | | 7/1985 | |
| DE | 0 186 019 A2 | | 7/1986 | |
| DE | 2822535 C2 | | 8/1988 | |
| DE | 0 651 635 B1 | | 5/1995 | |
| WO | WO 91/16085 | * | 10/1991 | ........... A61L/15/44 |
| WO | WO 96/22083 | | 7/1996 | |
| WO | WO 98/01167 | | 1/1998 | |
| WO | WO 98/54268 | | 12/1998 | |

* cited by examiner

Primary Examiner—Thurman K. Page
Assistant Examiner—Micah Paul Young
(74) Attorney, Agent, or Firm—Norris McLaughlin & Marcus

(57) ABSTRACT

An active substance matrix patch for controlled delivery of nonsteroidal antirheumatics to the skin, comprising a flexible cover layer and a water insoluble, pressure sensitively adhesive active substance matrix, wherein said adhesive matrix is free from mineral oils and tackifier resins and is composed of
a) from 25 to 90% by weight of synthetic framework polymers based on polyisobutylene,
b) from 5 to 40% by weight of amorphous poly-α-olefin,
c) from 10 to 60% by weight of an insoluble hydrophilic filler having an average particle size of less than 100 µm, and
d) from 0.001 to 20% by weight of a drug.

12 Claims, 1 Drawing Sheet

Effect of nature and amount of filler on the quality of skin bonding

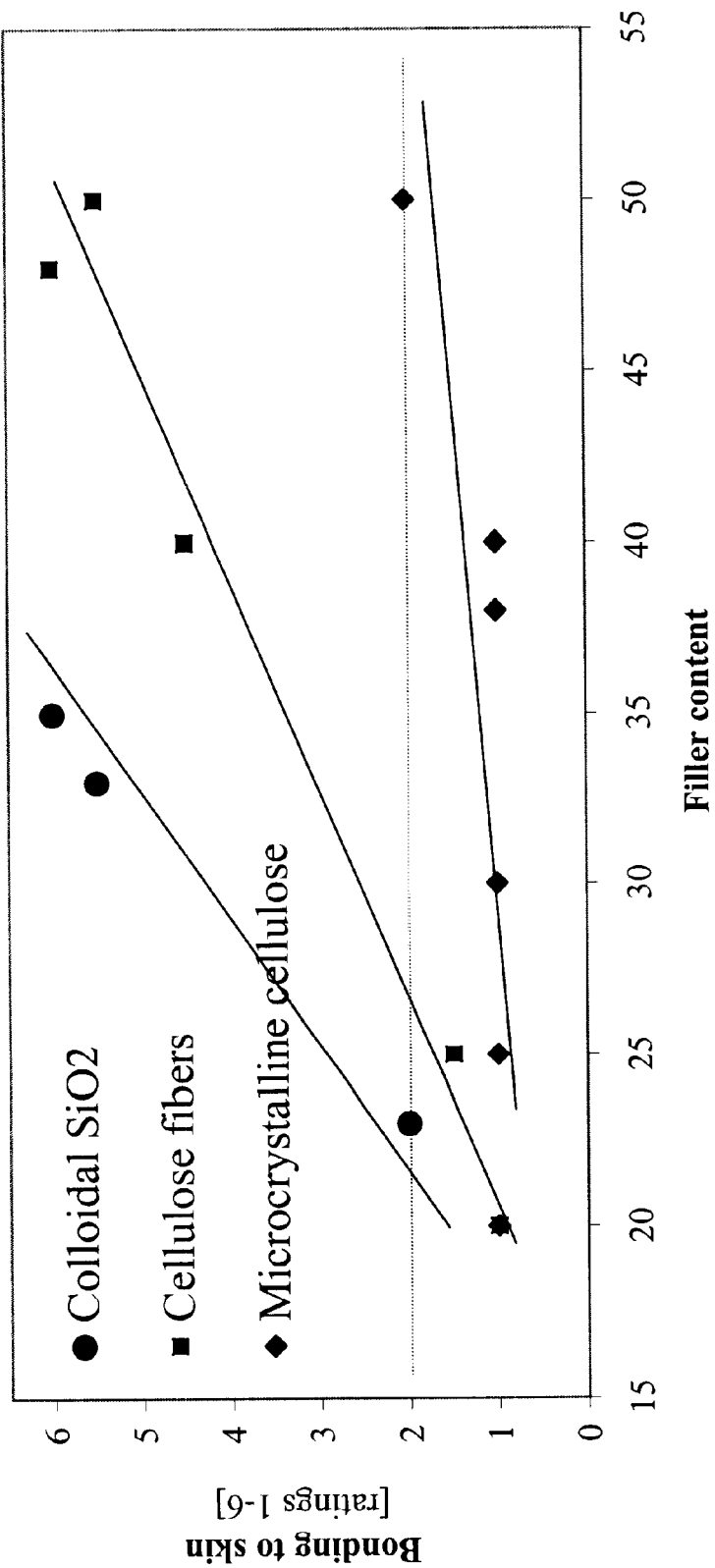

ACTIVE SUBSTANCE PATCH, KIND TO THE SKIN, FOR TRANSDERMAL ADMINISTRATION OF NONSTEROIDAL ANTIRHEUMATICS

The invention relates to a drug patch system based on synthetic rubbers for delivering at least one nonsteroidal antirheumatic for absorption through the skin over a period of up to 24 h, and to a process for producing it.

Transdermal therapeutic systems (TTS) for delivering active substances through the skin have been known for a long time. The topical application of drugs by way of active substance patch systems offers two main advantages. Firstly, this form of administration produces first order release kinetics of the active substance, thereby enabling a constant level of active substance to be maintained in the body over a very long period. Secondly, the path of uptake through the skin avoids the gastrointestinal tract and also the first liver passage. As a result, selected drugs may be effectively administered in a low dose. This is particularly advantageous when the drug is desired to act locally while avoiding a systemic effect. This is the case, for example, with the treatment of rheumatic joint complaints or muscular inflammation.

One embodiment of such transdermal systems which has been well described in the technical literature is that of matrix systems or monolithic systems in which the drug is incorporated directly into the pressure sensitive adhesive. In the ready-to-apply product, a pressure sensitively adhesive matrix of this kind, comprising active substance, is equipped on one side with a backing impermeable to the active substance, while on the opposite side there is a backing film equipped with a release layer, which is removed prior to application to the skin (kleben&dichten, No. 42, 1998, p. 26 to 30).

A fundamental requirement of a TTS is very good adhesion to skin, which must be maintained over the entire duration of the intended dosing of active substance. A frequently observed side effect, however, is the appearance of skin irritations, which occur in particular when a TTS is applied for a relatively long period, or repeatedly, to the same body region. The principal cause of these irritations are the ingredients of the pressure sensitively adhesive matrix. Painful redetachment of the active substance patch following a prolonged period of wear is a further observation.

Repeated and long-lasting applications of pressure sensitively adhesive systems to the same regions of the human body are encountered above all in the area of ostomy care. In this utility, hydrocolloids have long been used with great success as pressure sensitive adhesives. They consist in principle of a hydrophobic, pressure sensitively adhesive polymer matrix based on synthetic rubbers, dispersed in which matrix there are insoluble hydrophilic fillers based on, for example, alginates, cellulose or pectins. In the development of hydrocolloids for ostomy care, however, the primary requirements are the adhesion properties to wet skin and the ability to absorb liquid.

As long ago as 1967, U.S. Pat. No. 3,339,546 described a hydrocolloid based on polyisobutylenes for use in the oral cavity. A great disadvantage of the early systems was the deficient integrity of the matrices, i.e., the dissolution and breakup of the pressure sensitively adhesive matrix on absorption of relatively large amounts of liquid.

Later developments therefore aimed to solve this problem, and a number of proposed solutions are described in the literature. U.S. Pat. No. 4,393,080, for example, describes a hydrocolloid system based on elastomers, which uses high molecular mass hydrophilic fillers which promote the cohesion of the system even when swollen.

Further patents describe solutions by way of the crosslinking of the elastomer matrix, which may take place either physically or chemically.

Physical crosslinking, for example, may be effected by using phase separating block polymers based on poly (styrene-b-isoprene-b-styrene) (SIS), poly(styrene-b-isoprene-b-styrene) (SBS) or poly[styrene-b-(ethylene-stat.-butylene)-b-styrene] (SEBS). One of the first such systems is described, for example, in DE 28 22 535.

Chemical crosslinking may be effective, for example, by electron beam treatment or γ irradiation of the hydrocolloid matrix. A prerequisite for this is the presence in the pressure sensitively adhesive matrix of a sufficient number of reactive structural elements. This can be achieved, for example, as described in U.S. Pat. No. 4,477,325, by compounding with an ethylene-vinyl acetate copolymer.

Within the abovementioned inventions, although the technical problem of the cohesiveness of swollen hydrocolloids is described and solved, the problem of skin irritation as a result of repeated application is not addressed.

In contrast, WO 98/01167 does deal with skin irritations that may occur. In this case, aloe vera extract is used in order to prevent inflammatory skin changes and infection in the context of ostomy care. The system described, however, merely comprises a low molecular mass polyisobutylene as the polymer framework, and so the above-described problem of the cohesiveness of the hydrocolloid matrix continues to exist. Moreover, the composition described uses tackifier resins, whose allergenic potential is known.

Information regarding the suitability of such a system for the controlled delivery of drugs is present neither in this nor in any other of the abovementioned documents.

Transdermal therapeutic systems are generally applied to healthy, intact skin. In this case in particular it is especially important that the intact skin is not irritated, let alone damaged, by a drug. Furthermore, sufficient cohesiveness is necessary in order to be able to remove the active substance patch without residue after the period of wear is at an end.

Polyisobutylenes have long been used as a framework substance in the compounding of pressure sensitive adhesives. Relative to other known elastomers, synthetic polymers based on isobutylene offer a number of advantages. Owing to their synthetic production, they are free from unwanted ingredients; owing to their complete saturation they are highly stable to oxidation; and their inherent tack can be adjusted depending on molecular weight.

For application to skin in particular, therefore, they are preferred over other elastomers. For example, the allergenic potential of natural rubber, deriving from its natural impurities, is well known. Other synthetic rubbers based on styrene and isoprene and/or butadiene are very oxidation sensitive, necessitating the complicated addition of additives. Their hydrogenated derivatives based on poly[styrene-b-(ethylene-stat-propylene)-b-styrene] (SEPS) or poly[styrene-b-(ethylene-stat-butylene)-b-styrene] (SEBS), although more stable to oxidation, nevertheless lack inherent tack. Because of this, they additionally require compounding with tackifier resins in order to be used as pressure sensitive adhesives, as is described, for example, in EP 0 651 635 B1. These resins are generally very poorly defined mixtures of substances, frequently based on rosin. Consequently, here again an allergenic potential can not be ruled out.

The use of polyisobutylenes for transdermal therapeutic systems was described back in 1983 in DE 33 47 278 and DE 33 47 277. There, however, their use was always described in combination with either olefinic diene rubbers or tackifier resins, which again have the disadvantages described above. The use of amorphous poly-a-olefins as additives is also described, but without elucidating their effect on the overall system. The use of fillers is not mentioned in this description.

The use of PIB for transdermal systems without the addition of tackifier resins is described in U.S. Pat. No. 4,559,222. In that case, however, it is necessary to use very large amounts of mineral oil, the ratio of mineral oil to PIB in accordance with that invention being at least 1. Moreover, the system is restricted to active substances which are of moderate solubility in mineral oil. As a result, there is a further softening effect on the matrix. Fillers used comprise at least 6% by weight of colloidal silica. Regarding this ingredient, it is known that the antiadhesive properties of a release film are significantly disrupted by the use of silica.

WO 96/22083 describes a system for the transdermal administration of nicotine which operates on the basis of polyisobutylene without the addition of mineral oil. In this case, however, the necessary tack of the adhesive composition is achieved through the use of tackifier resins. These have the abovementioned disadvantages with respect to skin compatibility. A plasticizing effect, which has an additional positive effect on the adhesive properties of the matrix, is achieved by way of the active substance which is soluble in the PIB matrix. This compounding principle, however, greatly restricts the selection of active substances which can be administered by way of this matrix.

A system for the transdermal administration of drugs, based on polyisobutylenes without the use either of tackifier resins or of mineral oil, is described by U.S. Pat. No. 5,508,038. The central component for achieving sufficient adhesive properties in this case too, however, is the active substance, which in accordance with that invention must be oily and of ready solubility in the nonpolar matrix. This constitutes a very severe restriction, ruling out the use of nonsteroidal antirheumatics in this context. The system described is free from organic and inorganic fillers.

U.S. Pat. No. 5,508,038 is the only one of the cited publications to address the problem of skin irritation through the possible use of tackifier resins.

The use of amorphous poly-a-olefins in pressure sensitive adhesives in general is known in the literature. U.S. Pat. No. 4,186,258 is one of the first documents which designates the use of this class of substance in the field of hot-melt pressure sensitive adhesives. This document does not state a specific field of use.

U.S. Pat. No. 5,262,216 describes the use of these materials together with tackifier resins as hot-melt pressure sensitive adhesives, specifically for use on self-adhesive labels. Qualities of this class of polymer that are particularly praised here are the outstanding UV and aging resistance. There is no mention of their use on the human body.

WO 98/54268, in contrast, specifically describes the use of amorphous poly-α-olefins for applications on human skin. Moreover, in this case amorphous poly-α-olefins are used in combination with fillers. However, the field of use described is specifically that of wound covering. In this application, a particular feature of amorphous poly-α-olefins is their outstanding radiation resistance, as a result of which, in accordance with that invention, it is possible to produce readily sterilizable woundcare products. Additionally, amorphous poly-α-olefins are used here in combination with tackifier resins. Overall, the aspect of reduced skin irritation is not mentioned. Moreover, WO 98/54268 contains no indications that such a system is suitable for delivering drugs via the human skin. This document completely excludes the field of use of transdermal therapeutic systems.

The systems described to date for the transdermal administration of an active substance do not include organic fillers. However, these fillers in particular are responsible for the kindness to skin of the aforementioned pressure sensitive adhesives for ostomy care. By virtue of these fillers, moisture released by the skin during the period of wear of the patch can be absorbed very effectively. The resulting climate below the patch leads to a marked reduction in the incidence of skin maceration.

An invention of an active substance patch using water swellable fillers is described by EP 0 186 019 A1. In that case, however, the positive influence of the organic filler on the release rate of the active substance is described. The filler content in accordance with that invention is limited to 30% by weight. The aspect of the reduction of skin irritation is not addressed. Moreover, the systems described are realized using tackifier resins.

As remarked above, the realization of pressure sensitive adhesive systems for the transdermal administration of active substances, based on polyisobutyl without either tackifier resins or mineral oil, is described only for those drugs which possess an oily consistency at room temperature and/or which are soluble in the matrix. Consequently, the use of nonsteroidal antirheumatics, such as ibuprofen and ketoprofen, for example, is not possible on the basis of the known formulations, owing to the physical properties of these drugs. None of the tackifier resin free formulations described contains a hydrophilic filler.

It is an object of the present invention to develop, for the purpose of controlled delivery of a drug from the group of the nonsteroidal antirheumatics, a hydrocolloid system which not only possesses excellent cohesiveness but is also composed of components which are particularly kind to the skin and can be realized without any need at all for skin irritant components such as tackifying resins, for example. Furthermore, a production process is planned which operates without any solvent whatsoever, and, furthermore, the abovementioned side effects of a pressure sensitive adhesive for transdermal systems—skin irritations and painful redetachments—are avoided, resulting in a significant increase in wear comfort for the patient.

The object is to provide a matrix system which is based on polyisobutylene and which can be realized in a solvent free production process without conventional tackifier resins and mineral oil.

This object is achieved by an active substance matrix patch as claimed in the main claim. The subclaims relate to advantageous embodiments of the patch of the invention. Furthermore, the invention embraces processes for producing such patches.

The invention accordingly provides an active substance matrix patch for controlled delivery of nonsteroidal antirheumatics to the skin, comprising a flexible cover layer and a water insoluble, pressure sensitively adhesive active substance matrix, said adhesive matrix being free from mineral oils and tackifier resins and being composed of a) from 25 to 90% by weight of synthetic framework polymers based on polyisobutylene,
b) from 5 to 40% by weight of amorphous poly-a-olefin,
c) from 10 to 60% by weight of an insoluble hydrophilic filler having an average particle size of less than 100 pm, and
d) from 0.001 to 20% by weight of a drug.

In a first advantageous embodiment of the active substance matrix patch, the polyisobutylene is composed of from 5 to 30% by weight of high molecular mass PIB and from 20 to 60% by weight of low molecular mass PIB.

A typical pressure sensitive adhesive of the invention accordingly comprises the following

| | | |
|---|---|---|
| high molecular mass PIB | 5–30% by weight | preferably 10–20% by weight |
| low molecular mass PIB | 20–60% by weight | preferably 30–50% by weight |
| amorphous poly-α-olefin | 5–30% by weight | preferably 5–20% by weight |
| hydrophilic filler | 20–60% by weight | preferably 30–50% by weight |
| drug | 0.001–20% by weight | preferably 1.0–5.0% by weight |

Optionally, up to 20% by weight of a permeation enhancing auxiliary may also be added.

There follows a more precise definition of the abovementioned formulation constituents:

High molecular mass PIB:

Polyisobutylene having a weight average molecular weight (Mw) of from 500 000 to 1 100 000, preferably between 650 000 and 850 000. Such polymers are available commercially, for example, under the trade name Oppanol B100 (BASF) or Vistanex MM-L80 (Exxon).

Low Molecular Mass PIB:

Polyisobutylene having a weight average molecular weight (Mw) of from 40 000 to 120 000, preferably between 60 000 and 100 000. Such polymers are available commercially, for example, under the trade name Oppanol B15 (BASF) or Vistanex LMMH (Exxon).

Amorphous poly-α-olefin:

Amorphous copolymers based on ethylene and propylene, butylene or 1-hexene. The preferred weight average molecular weight (Mw) is from 5 000 to 100 000, preferably between 10 000 and 30 000. Such polymers are available commercially, for example, under the trade name Eastoflex® (Eastman) or Vestoplast® (Hüls).

Hydrophilic Filler:

Cellulose based hydrophilic particles insoluble in the abovementioned polymer matrix. Preference is given to an average particle size of less than or equal to 100 μm with a surface which is as uniform as possible. Such materials are available commercially, for example, under the trade names Avicel (FMC) and Elcema (Degussa-Hüls).

The active substance matrix is preferably produced in a process in which all of the components of the pressure sensitively adhesive matrix are homogenized in the melt without the addition of solvent.

With particular preference, all components are processed in a continuous or batchwise process at a temperature below 100° C.

The matrix is notable for outstanding adhesion properties on the skin, by easy and painless redetachability, and in particular by its extremely low potential to induce skin irritation. The production process does not use any solvents at all.

If desired, the open adhesive side—that to be applied to the skin—may be lined with a redetachable, covering protective layer.

As far as the selection of the fillers is concerned, it has surprisingly been found that particularly suitable fillers are those based on cellulose which possess an isotropic form and do not tend to swell on contact with water. Of these, fillers having a particle size of less than or equal to 100 μm are particularly suitable.

The use of hydrophilic fillers in a nonpolar matrix is known in the literature. They are described explicitly for use in transdermal therapeutic systems in EP 0 186 019. In that case, however, they are used only in a concentration of from 3 to 30% by weight, and no details of these fillers are given. Experience shows that systems having a filler content of more than 30% by weight suffer a significant loss of tack and become hard and brittle. In so doing, they lose the fundamental qualities required of a transdermal therapeutic system.

In the context of the present invention, however, it has been possible to show that fillers based on microcrystalline or amorphous cellulose can be used in substantially higher concentrations, without adversely affecting the adhesive properties, when they possess an isotropic form with a particle size of not greater than 100 μm. Larger amounts of fillers are desirable for improving the wear properties, especially in the case of long-lasting and repeated application.

The hydrophilic fillers known from the materials for ostomy care are integrated into the matrix of the invention, which serves to assist in skin compatibility.

The objective—the topical application of drugs from the group of the nonsteroidal antirheumatics, with or without the assistance of highly skin compatible additives—may be assisted in the context of the present invention by the addition of permeation enhancing auxiliaries such as, for example, fatty acid esters.

Surprisingly, it is possible to realize the abovementioned requirements in particular by means of a system which besides polyisobutylenes comprises amorphous poly-α-olefins in combination with amorphous or microcrystalline cellulose. The polymer basis of this simple system exclusively comprises synthetic ingredients whose quality can be monitored very effectively. As a result, allergenic reactions can largely be ruled out. The complete absence of poorly defined ingredients such as natural rubber or tackifier resins, for example, leads, as a result, to matrices which are particularly kind to the skin. The adhesive properties of the formulation of the invention, furthermore, can be adjusted very effectively. Moreover, there is no need for additional, stabilizing additives in the system. As already indicated, nonsteroidal antirheumatic topical application systems which are particularly kind to the skin can be realized on the basis of polyisobutylenes using amorphous poly-a-olefins and also cellulose particles as a filler.

The particular advantage of this raw material base lies in the exclusive use of fully saturated synthetic elastomers. These are highly defined and characterized, so making it possible to rule out contamination with accompanying allergenic substances. Because of the high degree of saturation, these polymer are highly stable to oxidation. As a result, there is no need for the extra addition of antioxidants and other stabilizers. The use of such additives, as is necessary when using natural rubber or unsaturated synthetic rubbers, always harbors the danger of skin incompatibility, owing to the chemical structure of the additives most commonly used. In addition, they represent an additional cost factor.

Furthermore, all of the elastomers used possess an inherent tack, depending on the molecular weight. As a result, it is also possible to forego the use of tackifier resins. Tackifier resins are frequently mixtures of substances, prepared on the basis of rosin, which are very poorly defined. A uniform structural formula can be given only in the rarest of cases. This makes it difficult to use tackifier resins as raw materials in drugs requiring approval, as in the present case of the transdermal therapeutic systems.

Because of the molecular weight dependent adhesion capacity on skin both of the polyisobutylenes and of the amorphous poly-a-olefins, the adhesive properties of the system of the invention may be adjusted within a very wide range without having to alter the chemistry of the base components. Often, a slight variation in the percentage proportions of the basic components is enough to give desired product properties.

This aspect is very important especially within drug development. The careful selection of unobjectionable raw materials possessing good skin compatibility is costly and time consuming. It is therefore desirable to be able to make specific adjustments to product properties by varying the percentage composition of the known raw materials, thereby obviating the time consuming replacement of a complete raw material.

EXAMPLES

Examples 1–17

To examine the effect of different ingredients of the pressure sensitively adhesive matrix in respect of the adhesion to skin, 17 comparative formulations were prepared as part of a statistical test plan.

The adhesion properties of the adhesive composition systems on skin was tested in a wear test by 6 volunteer subjects. Therefore, first of all, the drug was not incorporated. The specimens were evaluated in accordance with a rating system on a scale from 1 to 6, with 1 being the best evaluation and 6 the worst.

The laboratory specimens were produced in accordance with the following general procedure:

The stated amount of Vistanex MM L80 was charged at a temperature of 100° C. to a laboratory kneading machine equipped with Duplex blades and was kneaded for one hour until the material was in the form of crumbs. Subsequently, the stated amounts of Vistanex LM MH, tackifier resin and amorphous poly-a-olefin were added in succession and the material was kneaded for a further hour until homogeneous. Finally, the filler was added in the stated amount and kneading was continued for an hour. After it had cooled, the material was removed from the kneading machine.

Thereafter, the composition was pressed to a thickness of 500 μm between siliconized paper using a heated press at approximately 120° C. These specimens were laminated on one side with a polypropylene backing layer and on the side opposite this layer were lined with a siliconized polyester film.

Specimens measuring approximately 2.0×6.0 cm² with the form of standard commercial plaster strips were punched from this composition.

The specimens thus produced were stuck by the subjects to the inside of the forearm and worn for a period of 6 h. Assessments were made of the initial tack of the specimens on skin and also the adhesion capacity of the specimens over a period of 6 h.

Table 1 contains the exemplary formulations 1 to 17 processed in accordance with this procedure.

TABLE 1

Exemplary formulations 1–17

|  | PIB I | PIB II | Modifier | Filler |
|---|---|---|---|---|
| Example 1 | 17.0 | 30.0 | 5.0/I | 48.0/I |
| Example 2 | 20.0 | 50.0 | 5.0/I | 25.0/I |
| Example 3 | 10.0 | 30.0 | 20.0/II | 40.0/I |
| Example 4 | 10.0 | 50.0 | 20.0/III | 20.0/I |
| Example 5 | 17.0 | 43.0 | 20.0/III | 20.0/I |
| Example 6 | 7.0 | 38.0 | 5.0/IV | 50.0/I |
| Example 7 | 10.0 | 30.0 | 20.0/I | 40.0/II |
| Example 8 | 7.0 | 50.0 | 5.0/II | 38.0/II |
| Example 9 | 20.0 | 50.0 | 5.0/II | 25.0/II |
| Example 10 | 7.0 | 38.0 | 5.0/III | 50.0/II |
| Example 11 | 17.0 | 43.0 | 20.0/IV | 20.0/II |
| Example 12 | 20.0 | 30.0 | 20.0/IV | 30.0/II |
| Example 13 | 7.0 | 50.0 | 20.0/I | 23.0/III |
| Example 14 | 17.0 | 30.0 | 20.0/II | 33.0/III |
| Example 15 | 20.0 | 30.0 | 5.0/III | 45.0/III |
| Example 16 | 10.0 | 50.0 | 5.0/IV | 35.0/III |
| Example 17 | 14.0 | 39.0 | 12.0/IV | 35.0/III |

The following raw materials were used:

PIB I: Polyisobutylene, Vistanex MM L80, Exxon Chemical
PIB II: Polyisobutylene, Vistanex LM MH, Exxon Chemical Modifying Ingredients:

I: Aliphatic/aromatic hydrocarbon resin, Escorez 2101, Exxon Chemical
II: Hydrogenated polycyclopentadiene resin, Escorez 5300 1, Exxon Chemical
III: Hotmelt Adhesive, Duro Tak H 1540, National Starch
IV: Amorphous poly-a-olefin, Eastoflex E 1003, Eastman Fillers:

I: Cellulose fibers, JustFiber, International Filler of Belgium
II: Microcrystalline cellulose, Avicel PH 101, FMC
III: Colloidal silica, HiSil, PPG Industries The adhesive properties on the skin of the specimens thus produced were evaluated in accordance with a rating system of 1 to 6. In this system, 1 represents the best rating that can be awarded, 6 the worst. The results of this wear test are compiled in Table 2 and depicted graphically in FIG. 1.

TABLE 2

Evaluation of skin bonding

| Formulation | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|
| Evaluation | 6 | 1.5 | 4.5 | 1 | 1 | 5.5 | 1 | 1 | 1 | 2 | 1 | 1 | 2 | 5.5 | ./. | 6 | 6 |

(./.: no measurable adhesion to skin)

The figure clearly indicates that the nature and amount of the filler dominate the adhesive properties of the systems. Below an amount of approximately 20–25% by weight, all systems exhibit adhesion properties which are evaluated as being at least ugoodn (2.0), irrespective of the filler used. This situation alters drastically if the amount of filler is raised to more than 30% by weight.

Above a filler content of 30% by weight, very good adhesion properties are exhibited by those systems which in accordance with the invention use cellulose having an average particle size of 50 μm.

Example 18

To examine the active substance release of a system of the invention, a laboratory sample is prepared on the basis of the following formulation, in accordance with the general preparation description.

| | |
|---|---|
| Vistanex LM MH: | 32.40% |
| Vistanex MM L80: | 16.80% |
| Eastoflex PLS E1003D | 6.70% |
| Avicel PH 101: | 39.10% |
| Ibuprofen: | 5.00% |

5 samples with a diameter of 1.80 cm are punched from the laboratory specimen and examined for their release properties on pigs skin.

For this purpose, a sample is applied to a section of pig's skin which is placed on a Franz release vessel. The release vessel is filled with a receptor phase thermostated to a constant 35.5° C. and stirred continuously. The amount of ibuprofen in the skin and in the receptor phase is quantified at the time intervals indicated.

Results:

| Ibuprofen content [μg/cm$^2$] | 2 h | 4 h | 8 h | 24 h |
|---|---|---|---|---|
| Skin | 9.73 1.32 | 16.18 ± 1.68 | 23.80 ± 2.12 | 41.74 ± 6.02 |
| Receptor phase | 0.0 | 0.0 | 2.63 ± 0.54 | 25.66 ± 7.10 |
| Total | 9.73 ± 0.82 | 16.18 ± 0.64 | 25.55 ± 0.85 | 67.40 ± 8.22 |

What is claimed is:

1. An active matrix substance patch for controlled delivery of nonsteroidal antirheumatics to the skin, comprising a flexible cover layer and a water insoluble, pressure sensitive adhesive active substance matrix, wherein said adhesive matrix is free from mineral oils and tackifier resins and is composed of
   a) from 25 to 90% by weight of synthetic framework polymers based on polyisobutylene,
   b) from 5 to 40% by weight of amorphous poly-α-olefin,
   c) from 10 to 60% by weight of an insoluble hydrophilic filler having an average particle size of less than 100 μm, and
   d) from 0.001 to 20% by weight of a drug.

2. The patch as claimed in claim 1, wherein the matrix comprises poly-a-olefins in a concentration of from 5 to 20% by weight.

3. The patch as claimed in claim 1, wherein the polyisobutylene is composed of
   from 5 to 30% by weight of high molecular mass PIB, and
   from 20 to 60% by weight of low molecular mass PIB.

4. The patch as claimed in claim 1, wherein the filler is based on cellulose and its derivatives.

5. The patch as claimed in claim 1, wherein the matrix comprises a hydrophilic filler based on cellulose and its derivatives whose average particle size is in the range from 20 to 60 μm.

6. The patch as claimed in claim 1, wherein the matrix contains from 0.1 to 20% by weight of an active substance from the group of nonsteroidal antirheumatics.

7. The patch as claimed in claim 1, wherein permeation enhancing ingredients in the concentration range from 1.0 to 30% by weight, are added to the matrix.

8. A process for producing an active substance matrix patch as claimed in claim 1, wherein all components of the pressure sensitively adhesive matrix are homogenized in the melt without any addition of solvent.

9. The process as claimed in claim 8, wherein all components are processed in a continuous or batchwise process at a temperature below 100° C.

10. The patch as claimed in claim 6, wherein the matrix contains from 2 to 10% by weight, of an active substance selected from the group of nonsteroidal antirheumatics.

11. The patch as claimed in claim 6, wherein the nonstehoidal antirheumatic is selected from the group consisting of ibuprofen, ketoprofen, peroxicam, and diclofenac.

12. The patch as claimed in claim 7, wherein permeation enhancing ingredients in the concentration range from 10 to 25% by weight are added to the matrix.

* * * * *

UNITED STATES PATENT AND TRADEMARK OFFICE
CERTIFICATE OF CORRECTION

PATENT NO. : 6,652,876 B2
DATED : November 25, 2003
INVENTOR(S) : Radloff et al.

It is certified that error appears in the above-identified patent and that said Letters Patent is hereby corrected as shown below:

<u>Column 10,</u>
Line 8, "poly-a-olefins" should read -- poly-α-olefins --

Signed and Sealed this

Ninth Day of August, 2005

JON W. DUDAS
*Director of the United States Patent and Trademark Office*